Figure 1:
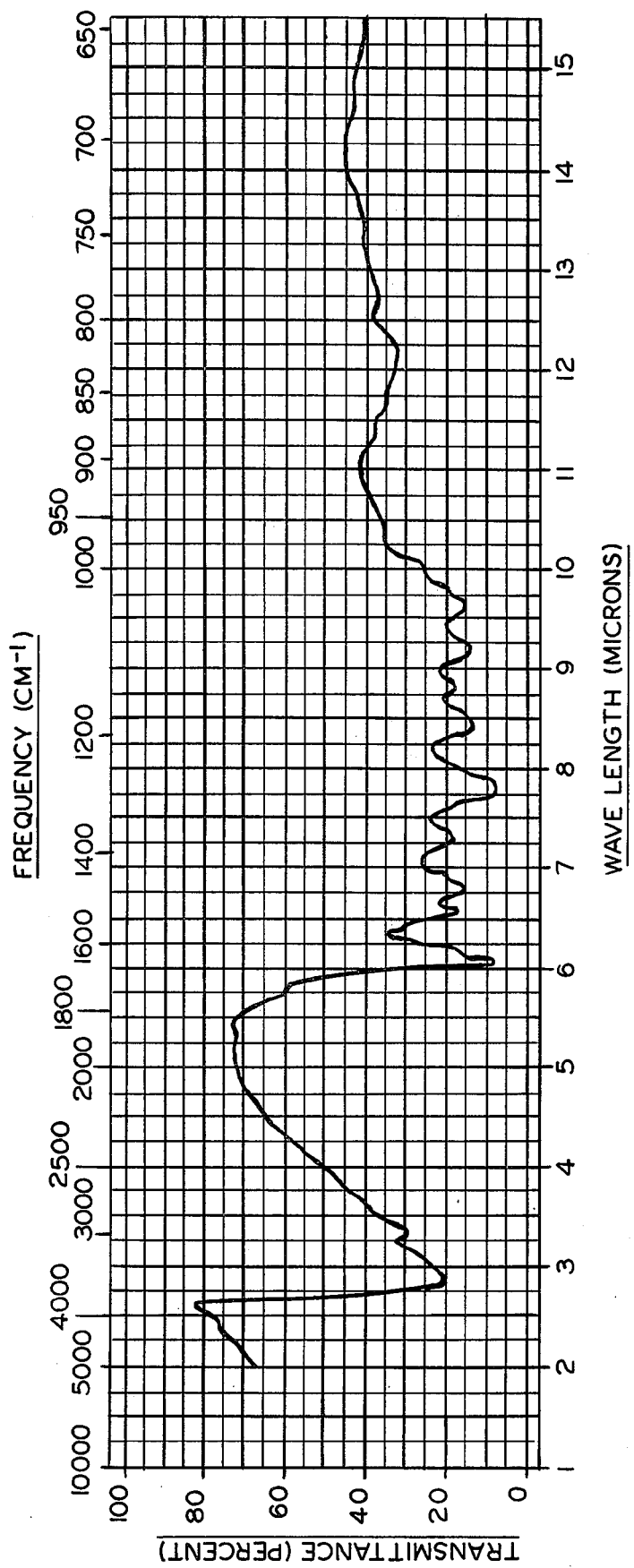

United States Patent [19]

Madaus et al.

[11] 3,994,925

[45] Nov. 30, 1976

[54] SALT OF THE SILYMARIN GROUP WITH AMINOPOLYHYDROXY ALCOHOLS

[75] Inventors: Rolf Hermann Heinrich Madaus, Cologne-Bruck; Günter Halbach, Cologne; Wilfried Trost, Bensberg-Frankenforst, all of Germany

[73] Assignee: Dr. Madaus & Co., Cologne am Rhine, Germany

[22] Filed: Jan. 21, 1974

[21] Appl. No.: 435,367

[30] Foreign Application Priority Data

Jan. 19, 1973 Germany.............................. 2302593

[52] U.S. Cl............................ 260/340.3; 260/345.2; 424/283
[51] Int. Cl.²................ C07D 311/30; C07D 311/22
[58] Field of Search............ 260/340.3, 345.5, 345.2

[56] References Cited

FOREIGN PATENTS OR APPLICATIONS

| | | | |
|---|---|---|---|
| 1,963,318 | 12/1969 | Germany | 260/340.3 |
| 1,057,349 | 2/1967 | United Kingdom | 260/345.5 |

OTHER PUBLICATIONS

Magliulo et al., Arzneim–Forsch, 23(1a), pp. 167–70, (Jan. 1973).
Abraham, et al., Index Chemicus, vol. 38, (1970) No. 155096.
Morrison et al., *Organic Chemistry*, (1966), 2nd Ed., pp. 801–803.
Industrie Biologique Francaise, S.A., C.A. 71:53556h, (1969).

*Primary Examiner*—Lorraine A. Weinberger
*Assistant Examiner*—Michael Shippen
*Attorney, Agent, or Firm*—Burgess, Dinklage & Sprung

[57] ABSTRACT

Salts of polyhydroxyphenylchromanones, e.g., silymarin or one or more members of the silymarin group, are reacted with a monoaminopolyhydroxy alcohol of the formula

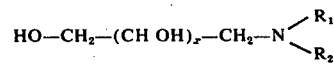

wherein
  x is an integer from 3 to 5; and
  $R_1$ and $R_2$ are hydrogen, lower alkyl or hydroxyalkyl to give chemotherapeutic salt compounds which are water soluble while retaining a high degree of medical effectiveness. The salt compounds can be administered to mammals to antagonize or mitigate liver damage and inflammation.

25 Claims, 2 Drawing Figures

FIG. I.

1-METHYLAMINO-GLUCOSE-SALT OF SILYMARIN

1-METHYLAMINO-GLUCOSE-SALT OF SILYMARIN
UV-SPECTRUM

SALT OF THE SILYMARIN GROUP WITH AMINOPOLYHYDROXY ALCOHOLS

The invention relates to new water-soluble salts of certain polyhydroxy phenyl chromanone compounds, for example of Silymarin or of the Silymarin group of chromanones. The instant salts have a protective and stabilizing effect upon the cellular and intracellular biomembranes, especially upon the liver cells, and are thus useful as therapeutic agents in the treatment of liver diseases.

It is known that the isolated polyhydroxy phenyl chromanones from the fruits of the milk thistle, *Silybum marianum*, which as a group are termed Silymarin, have a liver protective effect. (See, e.g., Halbach, G. und Görler, K. (Madaus) Planta Medica, 19 (4) 295 (1971); Offenlegungsschrift No. 1,767,666 (June 1, 1968), Dr. Madaus & Co.; Offenlegungsschrift No. 1,923,082 (May 6, 1969), Dr. Madaus & Co.; Hahn, G. and Mit. (Madaus) Arzneimittel-Forschung 18 698 (June 30, 1968); Rauen, H. M. und Schriewer, H., Arzneimittelforschung, 21 (8) 1194 (1971).) It is also known that the Silymarin group or Silymarin contains, inter alia, the following compounds:

"Silymarin I"

(See, e.g., Pelter, A. and Hänsel, Tetrahedron Letters, 25 2911 (1968); Wagner, H., Hörhammer, L. und Munster R., Arzneimittel-Forschung, 18, 688 (1968); Offenlegungsschrift No. 2,020,407 (April 27, 1970).)

"Silymarin II"

(See, e.g., Abraham, D. J. Wagner H. und Mit. Tetrahedron Letters, 31 2675 (1970); Halbach, G. und Görler, K. (Madaus) Planta Medica, 19 (4), 295 (1971).

Silymarin III (or Silychristine)

(See, e.g., Halbach, G. und Görler, K. (Madaus) Planta Medica, 19 (4), 295 (1971); Wagner, H. und Mit. Tetrahedron Letters, 22 1895 (1971).) In addition, there have been described partial half-esters of the Silybin (also referred to as Silymarin I) (see DAS No. 1,963,318) which, though water-soluble, cause a change in the Silybin molecule.

The polyhydroxy phenyl chromanones from the fruits of the milk thistle, i.e. the Silymarin group or Silymarin, are already being successfully used in liver therapy with a protective and stabilizing effect upon the cellular and intracellular biomembranes at the locations of the cytometabolism, especially upon the liver cells (see Offenlegungsschrift No. 1,767,666 (June 1, 1968), Dr. Madaus & Co.; Offenlegungsschrift No. 1,923,082 (May 6, 1969) Dr. Madaus & Co.; Hahn, G. und Mit. (Madaus) Arzneimittel-Forschung, 18 698 (June 30, 1968).) These compounds, however, have a low water-solubility and this limits their application in many pathologically serious and acute cases, where administration of the therapeutant needs to be made in the form of injections or intravenously.

There has been a need to produce a specific polyhydroxy phenyl chromanone materials, for example of the Silymarin group or Silymarin, which are in water-soluble form while retaining assured medical effectiveness. The conventional solubilizers do not fulfill this function because either their tolerance is insufficient or the active moieties do not remain stable and lose effectiveness. It has also been attempted to change the Silymarin molecules themselves in such a manner that they become water-soluble. In this manner, water-solubility can be achieved by forming sodium salts of different acid polyesters of these chromanones, especially with a total esterification, for example, phosphates and sulfates. Such molecular changes in the Silymarin group, however, lead to a decrease of the desired pharmacological effectiveness. The water-soluble alkali salts of Silymarin have been tried but were found not stable in aqueous solution due to excessive, i.e., too high pH values.

The instant invention provides water-soluble compounds of certain polyhydroxy phenyl chromanones, for example those of the Silymarin group or of Silymarin, while maintaining their pharmacological effectiveness.

It has been found that certain polyhydroxy phenyl chromanones, for example of the Silymarin group or Silymarin can be converted to the water-soluble state by reacting same with certain monoamino polyhydroxyalkyl alcohols, while maintaining pharmacological effectiveness.

The invention comprises water-soluble salts of polyhydroxy phenyl chromanones, particularly of those polyhydroxy phenyl chromanones, and polyhydroxy phenyl chromanones partially hydrated in a phenyl group, which are bound via their phenyl groups to the aliphatic sidechain through at least one ether-like bond of a coniferyl radical (i.e., a radical containing the molecular structure of Coniferyl alcohol), whose sidechain double bond is saturated by addition. The water-soluble salts are formed by adding a monoamino polyhydroxy alcohol of the formula

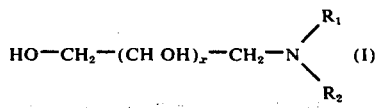

wherein $x$ is an integer from 3 to 5 and $R_1$ and $R_2$ are individually hydrogen, lower alkyl or lower hydroxyalkyl, e.g., of up to 6 carbon atoms. The resulting water-soluble compounds have a protective and stabilizing effect upon the cellular and intracellular biomembranes as the locations of the cytometabolism, especially on the liver cells, and are therefore particularly well suited as therapeutic agents to treat liver diseases.

The new water-soluble compounds become slightly hydrolized when left to stand for some time in aqueous solution. Therefore, in order to increase their stability over a longer period of time, in, for example, a salt-containing medium, specific physiologically harmless compounds can be added as stabilizers; e.g., polyvinyl pyrrolidone and physiological albumin may be thus employed. Polyvinyl pyrrolidone can be used in an amount of from 1 to 4% in the final preparation.

The active chromanone compounds whose salts are formed by invention can be obtained from the fruits of the milk thistle, Silybum marianum, as taught in U.S. Pat. No. 3,773,932, for example as follows:

1. The dried fruits of Silybum marianum (starting weight) are freed of the major amount of fatty oils on a screw press for oil seeds under high pressure. There results 75–80% of the starting weight of the press residue with a residual oil content of 5–10%.

2. The press residues (80% of the original weight) are exhaustively extracted with ethyl acetate. After having evaporated the ethyl acetate, there results about 5 to 6% (of the starting weight) of an oil-greasy, partially lumpy dry residue with an active material content of 20–30%.

3. 20 weight percent of the dry residue is dissolved in the lower phase of a system, brought to equilibrium, methanol/water (95 : 5 in volume) /petroleum ether (boiling range 40°–60° C) and from which flocculent solid materials have been removed by centrifuging to clarity. The end volume of the lower phase amounts to about three times as many liters as the number of the original weight of the fruits in kg.

4. Six individual centrifugal separators for liquid/liquid separation were arranged in series with one emulsifying stage inserted between each two centrifugers, so that the lower phase passes through the upper phase in counter-flow direction, whereby in each instance in the emulsifying stage both phases were emulsified one into the other so as to effect exchange of the material. In each following separator stage, the emulsion was again separated into heavy and light phases. The conduits are so arranged that the separated upper phase in countercurrent direction to the lower phase passes into each preceding emulsifying stage, etc. The upper and lower phases are first passed continuously against one another in the distribution battery without loading of substance, whereby the phase equilibrium establishes itself. The 20% solution of substance solution is then fed continuously into the flowing lower phase. On introduction at the inlet of the lower phase, it must be kept in mind that the total flowing volume ratio upper phase : lower phase = 1 : 1 must not be changed. The flow velocity of both phases depends extensively on the degree of efficiency of the emulsifying units on the separators. The optimum regulation can be ascertained gravimetrically by quantitative determinations of the transistion values of the material.

5. The lower phase leaving the distribution battery is dried in vacuo at 20 mm Hg and results in a yellow to beige-colored powder in a yield of 3.1 weight percent, calculated on the starting weight of the fruits. The content of active material (Silymarin or Silymarin group) is between 70 and 80%, with a yield of active material of 2.2%, calculated on the starting material.

The water-soluble, pharmacologically active salts of the invention are prepared by dissolving an amount of the specific polyhydroxy phenyl chromanone at boiling temperature under reflux in a volume of about eight times (in liters) of the weight (in kg) of the active chromanone, in an organic solvent, in which the Silymarin group material as well as the monoamino polyhydroxy alcohol are soluble. Suitable solvents are:

a. lower aliphatic alcohols, such as methanol, ethanol, etc.;

b. lower alkyl esters of lower aliphatic carboxylic acids;

c. lower aliphatic ketones.

To the still hot solution of the Silymarin group member there is added, while stirring, a hot solution of substantially equimolar amount of a monoaminopolyhydroxyalkyl alcohol of the formula

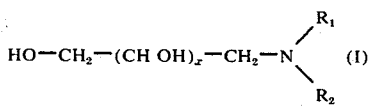

which is preferably dissolved in the same organic solvent (if another solvent is used, it must form a single phase with the first). The solvent is then completely distilled off under decreased pressure. Still adhering solvent residues are removed by drying for 20 to 60 hours at 30°–60° C in a vacuum drying chamber. The thus obtained beige-brown product is well soluble in water at room temperature up to 35–40%.

The 1-methylamino-glucose salts of the Silymarin group material are used for toxicological and pharmacological tests. The abbreviation "SMG1" (1-methylamino glucose is abbreviated as "MG1") is used for this water-soluble Silymarin preparation. SMG1 is stable in distilled water and, by adding 4% by weight of polyvinylpyrrolidone (of molecular weight of about 10,000), SMG1 achieves good stability also in 0.9% NaCl. The pH-value of the solution should not be below 7.6.

The acute toxicity and tolerance of SMG1 after intravenous injection was tested on mice, rats, rabbits, and dogs. The test animals received the SMG1 i.v. dosage in 0.9% NaCl solution, to which 4% PVP was added. Since PVP is not tolerated by dogs (which is not applicable to humans), these animals received SMG1, dissolved in twice distilled water. The $DL_{50}$ dosage amounts for the mouse were 560 mg/kg i.v. SMG1, and for the rat 540 mg/kg SMG1 i.v. The DL min. for the rabbit was to 200 mg/kg SMG1 i.v. and the dosage tolerance in dogs was 200 mg/kg i.v. SMG1. The liver-protective effect of the SMG1 was tested on white rats, in that experimentally produced liver damage was antagonized by SMG1 treatment. The rats were injected with the SMG1- or MG1-dosages in 5 ml 0.9% NaCl solution, to which 4% of PVP (M.W. about 10,000) was added per kg of body weight. A dosage of 140.5 mg/kg SMG1 corresponds to 100 mg Silymarin and 40.5 mg 1-methylamino-glucose. When the test animals received 140.5 mg/kg SMG1, the control animals were treated with the equivalent dosage of 1-methylamino glucose, i.e. 40.5 mg/kg.

Antagonization of $CCl_4$ induced liver damage by SMG1 was measured by the hexobarbital period of sleep. This experimental determination is based on the following: the period of sleep after administration of hexobarbital is appreciably determined by the speed at which the compound is chemically decomposed in the liver. Thus, the period of sleep seems prolonged (see W. Klinger: Arch. int. Pharmacodyn. 184, 5–18 (1970)) in animals with partially resected liver or chemically-damaged liver, e.g. by $CCl_4$ treatment. Pharmaceuticals with a liver protective effect will, therefore, counter the prolongation of the hexobarbital sleep (see D. Lenke Acta biol. med. germ. 3, 37–40 (1959)). Test animals were female Wister rats weighing approximately 200 g each. The liver damage was produced by oral administration of 0.2 ml/kg $CCl_4$. One hour prior to the $CCl_4$ liver damage, the test animals were treated i.v. with 140.5 mg/kg of 1-methylamino glucose (MG1) i.v. A control group with undamaged livers received 40.5 mg/kg MG1 at the same time. 48 hours after the $CCl_4$ liver damage, the hexobarbital period of sleep was determined in all animals after intraveneous injection of 50 mg/kg hexobarbital. The time from the end of the hexobarbital injection to the first independent arising and motorcoordinated forward movement of the animals was taken as criterion for the period of sleep. During sleep, the rats were placed under a heating lamp in order to prevent cooling.

| | control animals | $CCl_4$-damaged animals | $CCl_4$-damaged animals + Silymarin i.v. |
|---|---|---|---|
| Hexobarbital-period of sleep in minutes | 39.4 ± 2.32 n = 13 | 64.2 ± 2.67 n = 15 | 50.6 ± 4.26 n = 14 |
| Protective effect against the $CCl_4$ liver damage | | | 54.8% |

The prolongation of the period of sleep caused by $CCl_4$ was antagonized to 54.8% by the Silymarin i.v. treatment.

In another series of tests, antagonization of proseodymium nitrate liver damage by SMG1, measured by the reaction of the serum enzyme glutamate-oxalacetate-transaminase (GOT), glutamate-pyruvate-transaminase (GPT), sorbital-dehydrogenase (SDH) and alkaline phosphatases (AP), was employed as a measure of efficacy of the instant materials. Liver damage may be produced in rats by praseodymnitrate, which damage can result in a fatty liver (see Neubert D. and Hoffmeister I.: Naunyn-Schmiedebergs Arch. exp. Path. Pharmakol., 237, 519 (1960)). A SMG1 i.v. treatment prevents this liver damage. The test animals, male Wistar rats weighing approximately 200 g, were treated for three days with 140.5 mg/kg SMG1 i.v. On the first testing day, all rats were damaged i.v. with 14 mg/kg praseodymnitrate one hour after the SMG1- or MG1- injection. Seventy-two hours after the praseodymnitrate liver damage, the enzymes GOT, GPT, SDH and AP (by means of biochemical test combinations of Boehringer Mannheim GmbH) were determined in the serum and the lower level of these enzymes in the serum of the SMG1 treated animals was taken as a measure of successful antagonization of liver damage.

The results are set forth in the following table:

| Parameter | Control animals treated i.v. with 1-methylamino-glucose mU/ml | n | Test animals treated i.v. with SMG1 mU/ml | n |
|---|---|---|---|---|
| GOT | 360.6 | 44 | 105.2 | 42 |
| GPT | 118.4 | 44 | 28.2 | 42 |
| SDH | 32.0 | 28 | 3.2 | 30 |
| AP | 168.0 | 44 | 108.9 | 42 |

The calculations were carried out in accordance with the Wilcoxon test and the results show that the SMG1-treatment significantly antagonized praseodymnitrate induced liver damage, measured on the basis of the serum enzymes GOT, GPT, SDH and alkaline phosphatase. SMG1 i.v. additionally has an excellent liver protective effect against poisons such as $\alpha$-amanitine and phalloidine.

For treating patients with liver damage, the described salts can be administered enterally and here also parenterally in accordance with the methods of administration used for Silymarin itself, which are well-known in the art. The dosage ranges suitable for injections, calculated on Silymarin, are between 50 and 250 mg/day, i.e. 70–350 mg/day of SMG1, depending on the seriousness or the acuteness of the illness. In case of enteral application dosages between 100 and 500 mg, calculated on Silymarin, i.e. 140–170 mg/day of SMG1, are suitably employed.

In general, at the start of therapy ampoules are used and then over weeks or months it is further treated perorally.

The indications for SMG1 correspond to those of Silymarin: acute and chronic hepatitis, liver cirrhosis, toxic-metabolic fatty liver, posthepatitic conditions.

The evaluation of the therapeutic effect is made by the control of liver function samples, such as serum transaminases (SGOT,SGPT), bromsulphalein, alkaline phosphatase, iron, bilirubin, serum bilirubin spectrum, immunoglobuline, Australia-antigentiter, coagulation factors, as well as the histologic evaluation of tissue samples of the liver.

The improvement also expresses itself in the general health situation of the patient, lessening of the symptomatic of the epigastric region, increase of appetite and efficiency.

The following examples are additionally illustrative of the invention.

EXAMPLE 1

Preparation of SMG1

482 g of Silymarin were dissolved in four liters of boiling methanol under reflux. To the still hot solution there was added, while stirring, a hot solution of 195 g of 1-methylamino glucose in 2 liters of methanol. The solvent was then completely distilled off under decreased pressure. Still adhering solvent residues were removed by drying for 50 hours at 40°–50° C in a vacuum drying chamber. The thus obtained beige-brown product is up to 40% soluble in water at room temperature.

Figure 2:
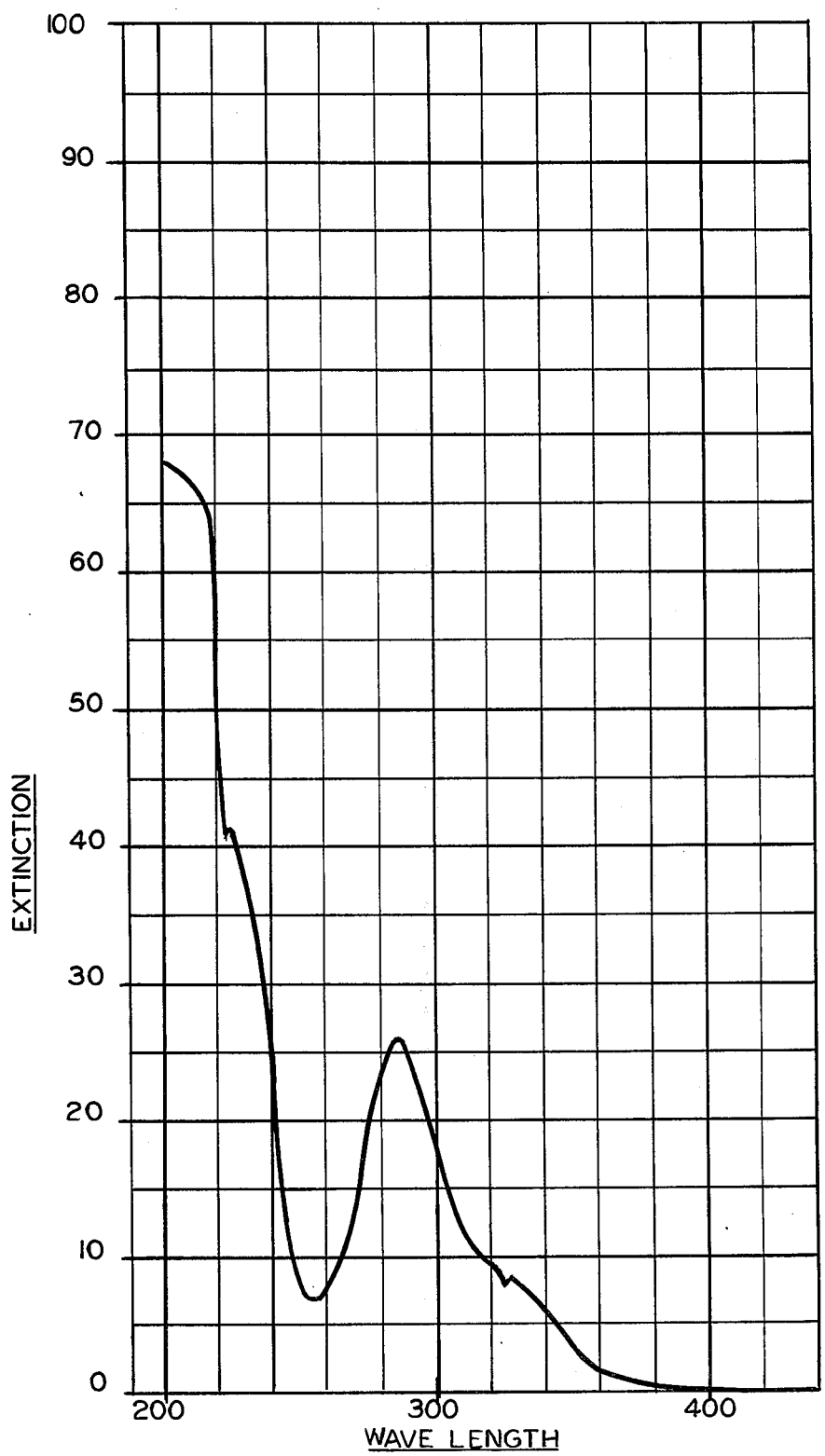

The IR- and UV spectra of this new composition are set forth in FIG. 1 and FIG. 2.

EXAMPLE 2

Preparation of 1-Aminoglucose salt of Silymarin 160 g of Silymarin were dissolved in 1.8 liters of ethanol under reflux. At the boiling point, there was added a solution of 60 g of 1-aminoglucose in 500 ml ethanol. The alcohol was completely distilled off under decreased pressure and the residue well soluble in water was freed of the remaining solvent at maximum 40°–50° C in the vacuum drying cabinet within 48 hours.

EXAMPLE 3

Preparation of 1-Ethanol-Amino Glucose Salt of Silymarin

At the boiling point, a hot solution of 112 g of 1-ethanol-amino glucose in 1.4 liters of methanol was added to a solution of 241 g of Silymarin in 2 liters of methanol. Afterwards, the entire methanol was distilled off under decreased pressure and the residue was dried at maximum 50° C in the vacuum cabinet within 50 hours.

Salts with monoaminopolyhydroxy alcohols of the general formula $HO\,CH_2-(CH\,OH)_x-CH_2-N-R_1\,R_2$ as set forth above can be made according to the methods of examples 1, 2 and 3.

PREPARATION OF THERAPEUTIC COMPOSITIONS

EXAMPLE A

Ampoules

For the preparation of 10,000 ampoules, 1,405 kg of SMG1 are dissolved in 48.6 liters of physiological sodium chloride solution, to which there were added 4% of polyvinyl pyrrolidone (M.W. about 10,000). The pH value should not be below 7.6. The solution is sterile filtered and is filled into sterile brown 5 ml ampoules, so that the content per ampoule amounts to 140.5 mg of SMG1 in accordance with 100 mg of Silymarin.

EXAMPLE B

Tablets and Dragees 49,175 kg of SMG1 are mixed with the following additives:
  3.2 kg microcrystalline cellulose
  8.7 kg amylum tritici
  171.675 kg lactose
and granulated with a PVP solution. There are added to the dried granulate:
  4.0 kg microcrystalline cellulose
  3.25 kg silica
  5.0 kg stearic acid
From the mixture tablets are pressed weighing 250.0 mg (containing 49.175 mg SMG1, corresponding to 35 mg of Silymarin). The comprimates can serve, in a given case, as cores for the dragee preparation.

They are coated with the following coating suspension in accordance with the conventional process:

| Gum arabic | 5.95 kg |
| Talcum | 81.55 kg |
| Chocolate-brown | 2.63 kg |
| Terra die Siena | 12.50 kg |
| Saccharose | 97.37 kg |

The final weight of a dragee is 450.0 mg.

EXAMPLE C

Tablets and Dragees 49,175 kg of SMG1 are mixed with the following substances:
65.500 kg glucose
16,440 kg Amylum tritici
3.500 kg Sorbite
1.250 kg polyethylene glycol-sorbitanum oleinicum
5.000 kg Stearic acid
109.135 kg Lactose
and are compressed to tablets, each tablet weighing 250 mg (containing 49.175 mg SMG1, corresponding to 35 mg of Silymarin). In a given case, the compressed tablets may serve as cores for the dragee preparation, using 200 kg of the above-mentioned coating suspension, so that each dragee weighs about 450 mg.

EXAMPLE D

Suppositories 196.7 g of SMG1 are rubbed with 500 mg of molten hard fat DAB 7. While stirring, 1,304 kg of molten hard fat DAB 7 are added and suppositories are cast from the mass. Each suppository of 2.0 g contains 196.7 SMG1 corresponding to 140 mg of Silymarin.

EXAMPLE E

Drops

In 67.285 kg of demineralized water, there are dissolved successively
1.000 kg of polyvinyl pyrrolidone (M.wt. =10,000)
2.810 kg of SMG1
0.200 kg of potassium sorbate
9.015 kg of saccharine.
Then there are added
28.570 kg of Karion F in liquid form
0.100 kg of chocolate aroma
0.020 kg of peppermint aroma.
The concentration of the solution is 2.81%, so that in 20 drops there are contained 28.1 mg SMG1 corresponding to 20 mg Silymarin.

It will be understood that the specification and examples are illustrative but not limitative of the present invention and that other embodiments within the spirit and scope of the invention will suggest themselves to those skilled in the art.

What is claimed is:

1. Salt of Silymarin group polyhydroxyphenylchromanone with a monoaminopolyhydroxy alcohol of the formula

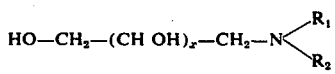

wherein
$x$ is an integer from 3 to 5; and
$R_1$ and $R_2$ are hydrogen, lower alkyl or lower hydroxyalkyl.

2. Salt as claimed in claim 1, wherein said monoaminopolyhydroxy alcohol is of the formula

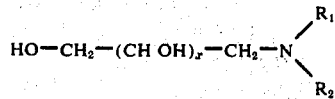

wherein
$x$ is an integer from 3 to 5; and
$R_1$ and $R_2$ are hydrogen, methyl or hydroxyethyl.

3. Salt as claimed in claim 1 wherein said Silymarin group polyhydroxyphenylchromanone is Silymarin I.

4. Salt as claimed in claim 1, wherein said Silymarin group polyhydroxyphenylchromanone is Silymarin II.

5. Salt as claimed in claim 1, wherein said Silymarin group polyhydroxyphenylchromanone is Silymarin III.

6. Salt as claimed in claim 1, wherein said Silymarin group polyhydroxyphenylchromanone is a mixture of Silymarin I, II and III.

7. Salt as claimed in claim 1, wherein said monoaminopolyhydroxy alcohol is 1-methylamino glucose.

8. Salt as claimed in claim 1, wherein said monoaminopolyhydroxy alcohol is 1-amino glucose.

9. Salt as claimed in claim 1, wherein said monoaminopolyhydroxy alcohol is 1-ethanolamino glucose.

10. Salt as claimed in claim 1, wherein $x$ in the formula is 3.

11. Salt as claimed in claim 1, wherein $x$ in the formula is 4.

12. Salt as claimed in claim 1, wherein $x$ in the formula is 5.

13. Salt as claimed in claim 1, wherein $R_1$ is hydrogen and $R_2$ is alkyl of up to 6 carbon atoms.

14. Salt as claimed in claim 1, wherein $R_1$ is hydrogen and $R_2$ is hydroxyalkyl of up to 6 carbon atoms.

15. Salt as claimed in claim 1, wherein $R_1$ and $R_2$ are hydrogen.

16. Salt as claimed in claim 1, wherein $R_1$ and $R_2$ are lower alkyl.

17. Salt as claimed in claim 1, wherein $R_1$ and $R_2$ are lower hydroxyalkyl.

18. Salt as claimed in claim 1, wherein $R_1$ is alkyl and $R_2$ is lower hydroxyalkyl.

19. Salt as claimed in claim 1, wherein said polyhydroxyphenylchromanone comprises at least one member of the Silymarin group consisting of Silymarin I, Silymarin II, and Silymarin III and the monoaminopolyhydroxy alcohol is selected from 1-amino-glucose, 1-methylamino glucose and 1-ethanolamino glucose.

20. Process for the preparation of a salt as claimed in claim 1, which process comprises contacting a polyhydroxyphenylchromanone with a monoaminopolyhydroxy alcohol of the formula

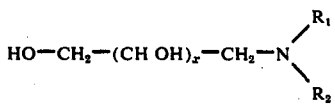

wherein
$x$ is an integer from 3 to 5; and
$R_1$ and $R_2$ are hydrogen, lower alkyl or lower hydroxyalkyl
in an organic solvent.

21. Process as claimed in claim 20, wherein said contacting is carried out under elevated temperature.

22. Process as claimed in claim 20, wherein the polyhydroxyphenylchromanone is dissolved in the solvent and the monoaminopolyhydroxy alcohol is dissolved in the same solvent and the two solutions are contacted with each other.

23. Process as claimed in claim 20, wherein said solvent is a lower aliphatic alcohol of up to 6 carbon atoms.

24. Process as claimed in claim 20, wherein said solvent is a lower alkyl ester of a lower aliphatic carboxylic acid.

25. Process as claimed in claim 20, wherein said solvent is a lower aliphatic ketone.

* * * * *